United States Patent
Shifflett et al.

(10) Patent No.: US 10,368,781 B2
(45) Date of Patent: Aug. 6, 2019

(54) DEVICE FOR MEASURING THE CIRCUMFERENCE OF A CHILD'S HEAD

(71) Applicants: Maureen Shifflett, Atlanta, GA (US); Sandra Griffin, Cumming, GA (US)

(72) Inventors: Maureen Shifflett, Atlanta, GA (US); Sandra Griffin, Cumming, GA (US)

(73) Assignees: Maureen Shifflett, Atlanta, GA (US); Sandra Griffin, Cumming, GA (US)

( * ) Notice: Subject to any disclaimer, the term of this patent is extended or adjusted under 35 U.S.C. 154(b) by 74 days.

(21) Appl. No.: 15/625,002

(22) Filed: Jun. 16, 2017

(65) Prior Publication Data

US 2017/0360330 A1 Dec. 21, 2017

Related U.S. Application Data

(60) Provisional application No. 62/350,770, filed on Jun. 16, 2016.

(51) Int. Cl.
*A61B 5/107* (2006.01)
*G01B 5/02* (2006.01)
*A61B 8/08* (2006.01)

(52) U.S. Cl.
CPC .............. *A61B 5/107* (2013.01); *G01B 5/025* (2013.01); *A61B 8/0808* (2013.01); *G01N 2800/28* (2013.01)

(58) Field of Classification Search
CPC ................................ A61B 5/107; G01B 5/025
USPC ..................................... 33/512, 555.1, 555.4
See application file for complete search history.

(56) References Cited

U.S. PATENT DOCUMENTS

| 1,672,913 | A | * | 6/1928 | Schaap | ............... G01B 5/025 33/542 |
| 3,918,166 | A | | 11/1975 | Mason | |
| 5,193,287 | A | | 3/1993 | Coulter et al. | |
| 5,269,069 | A | * | 12/1993 | Min | ............... G01B 5/025 33/514.1 |
| 5,732,475 | A | | 3/1998 | Sacks et al. | |
| 6,179,791 | B1 | | 1/2001 | Krueger | |
| 6,460,262 | B1 | * | 10/2002 | Cabak | ............... A61B 5/1076 33/511 |
| 6,612,048 | B2 | | 9/2003 | Peterlechner et al. | |

(Continued)

FOREIGN PATENT DOCUMENTS

EP 0959322 A2 11/1999

*Primary Examiner* — George B Bennett
(74) *Attorney, Agent, or Firm* — Merchant & Gould P.C.

(57) ABSTRACT

A measurement device for measuring the circumference of a human head. The measurement device includes a generally circumferential body that fits around a human head. The generally circumferential body has a receiver segment with an elongated geometry. The receiver segment includes an adjustment end receiver. The receiver segment is flexible. The generally circumferential body also has an adjustment segment with a measurement end. The adjustment segment measurement end has a diameter that is narrower than the receiver segment adjustment end receiver diameter. The adjustment segment has a measurement indicator that extends from the measurement end. The adjustment segment is flexible. The adjustment segment measurement end is adjustably inserted into the receiver segment sliding end receiver. The visual measurement indicator is operable with respect to the receiver segment adjustment end receiver.

20 Claims, 7 Drawing Sheets

(56) References Cited

U.S. PATENT DOCUMENTS

| | | | |
|---|---|---|---|
| 6,640,460 B1 | 11/2003 | Nabarro et al. | |
| 6,817,110 B2 | 11/2004 | Bohnengel | |
| 7,111,409 B2 * | 9/2006 | Janssen | B26B 29/06 33/21.1 |
| 7,225,554 B2 | 6/2007 | Madsen | |
| 7,578,070 B1 * | 8/2009 | Lynch | G01B 3/34 33/514.1 |
| 2002/0157273 A1 * | 10/2002 | Noyes | A41F 9/00 33/759 |
| 2002/0184779 A1 * | 12/2002 | Bohnengel | G01B 3/1056 33/555.4 |
| 2010/0081904 A1 | 4/2010 | Medina | |
| 2010/0240967 A1 * | 9/2010 | Kim | A61B 5/02055 600/301 |
| 2015/0201866 A1 * | 7/2015 | Wojcieszak | A43D 1/02 33/512 |
| 2015/0369579 A1 * | 12/2015 | Mathis | G01B 3/1082 33/701 |
| 2016/0302690 A1 * | 10/2016 | Nebuya | A61B 5/6831 |
| 2018/0188012 A1 * | 7/2018 | Chen | G01B 5/025 |

* cited by examiner

DEVICE FOR MEASURING THE CIRCUMFERENCE OF A CHILD'S HEAD

CROSS-REFERENCE TO RELATED APPLICATION

This application claims the benefit of U.S. Provisional Patent Application No. 62/350,770, filed Jun. 16, 2016, which is entirely incorporated herein by reference.

TECHNICAL FIELD

The present disclosure relates to a device for measuring the circumference of a human head.

BACKGROUND

The term head circumference (HC) refers to a measurement of an individual's occipital-frontal circumference, which is the largest circumferential measurement of the human head. HC is monitored routinely throughout infancy and early childhood. This measurement, similar to an infant or child's length and weight measurements, is plotted on a standardized growth chart rendering a percentile reading specific to that child's age and gender. If a child's head measures 75th percentile on the HC growth chart for girls ages 0-36 months, for instance, that means 75% of girls her same age have the same size or smaller head. The percentile reading is closely monitored by the pediatric primary care provider to assess the child's brain growth and development.

While genetics play an important role in head size, just as it does length and weight, an unexpected deviation from previous percentile will cue the provider to consider the cause. The first step is to question proper measurement technique and recheck. If accurate, parental head size is generally considered, as well as comprehensive neurological and developmental histories and exams conducted. A condition known as hydrocephalus, meaning water on the brain, for instance, is one explanation for a sudden increase in HC measurement. A smaller than expected measurement may be indicative that the child's brain is not developing properly.

Just like length and weight, a trained professional routinely obtains HC measurement at every well child visit throughout infancy and early childhood prior to the pediatric healthcare provider exam. Common practice involves use of a paper disposable or flexible plastic measuring tape which may coil back into a hard plastic case, a fixed loop tape in which one end overlaps the other, or folded/accordion-like tape, all which extend and retract with manual manipulation. Depending on the child's age, this measurement can be obtained with the infant lying on the exam table or infant/child sitting in the parent's lap. Either way, the nurse or medical assistant usually depends on the parent's assist to hold the infant or child's head still while he/she applies obtains the measurement. The examiner generally approaches the child from the front, extends the tape against the infant or child's occipital prominence, then wraps it around the frontal prominence to obtain a measurement. While this is a simple, non-invasive procedure, obtained HC measurements are often inaccurate. First, young children rarely tolerate this procedure. Young infants are squirmy, while older infants and toddlers often exhibit stranger anxiety and fight the procedure. To exacerbate their fear, the recoiling tape measure is often noisy and "clicks" when it extends, frightening a young child. Even in cases of a cooperative child, this procedure is cumbersome as the examiner attempts to hold the tape in place on the child's head while manually adjusting expanding the tape and maneuvering to read the measurement in centimeters. The tape easily slips off either boney prominence, resulting in an inaccurate measurement. Thus, the procedure is often repeated several times before obtaining an accurate measurement. It is a cumbersome, inefficient procedure that creates frustration for all involved, including patient, parent, examiner and provider. Further, when the same tape measure is used to measure other body parts (i.e., Elbow swelling resulting from infectious bacteria), this creates unnecessary risk for young infants and toddlers.

SUMMARY

Generally, aspects of the present disclosure relate to a measurement device that fits around a human (e.g., child) head to measure circumference. The measurement device generally has a pair of sections, including a receiver section and an adjustment section. The adjustment section has a measurement indicator to show circumference measurement. The receiver section has an adjustment receiver that slidably receives an end of the adjustment section, including the measurement indicator. In use, the adjustment section inserts into the receiver section adjustment receiver a distance that indicates the circumference of the head being measured.

Aspects of the present disclosure relate generally to a measurement device for measuring the circumference of a human head. The measurement device includes a generally circumferential body that fits around a human head. The generally circumferential body includes a receiver segment with an elongated geometry and an adjustment end receiver. The receiver segment is flexible. The generally circumferential body also includes an adjustment segment that has a measurement end. The adjustment segment is flexible. The adjustment segment measurement end includes a diameter that is narrower than the receiver segment adjustment end receiver. The adjustment segment measurement end is adjustably inserted into the receiver segment adjustment end receiver. The adjustment segment includes a measurement indicator that extends from the measurement end. The visual measurement indicator is operable with respect to the receiver segment adjustment end receiver. Optionally, the generally circumferential body can be a single structure, with the adjustment segment and receiver segment being parts of the same single structure. Optionally, the generally circumferential body can be formed of separable parts, with the adjustment segment and the receiver segment being separably connected to each other.

DESCRIPTION

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

FIGS. 1-8 illustrate a measurement device for measuring the circumference of a human head. The illustrated measurement device includes a generally circumferential body 100 that fits around a human head. The generally circumferential body 100 is made of antimicrobial plastic. The generally circumferential body 100 can have a general D-shape circumference.

Figure 3:
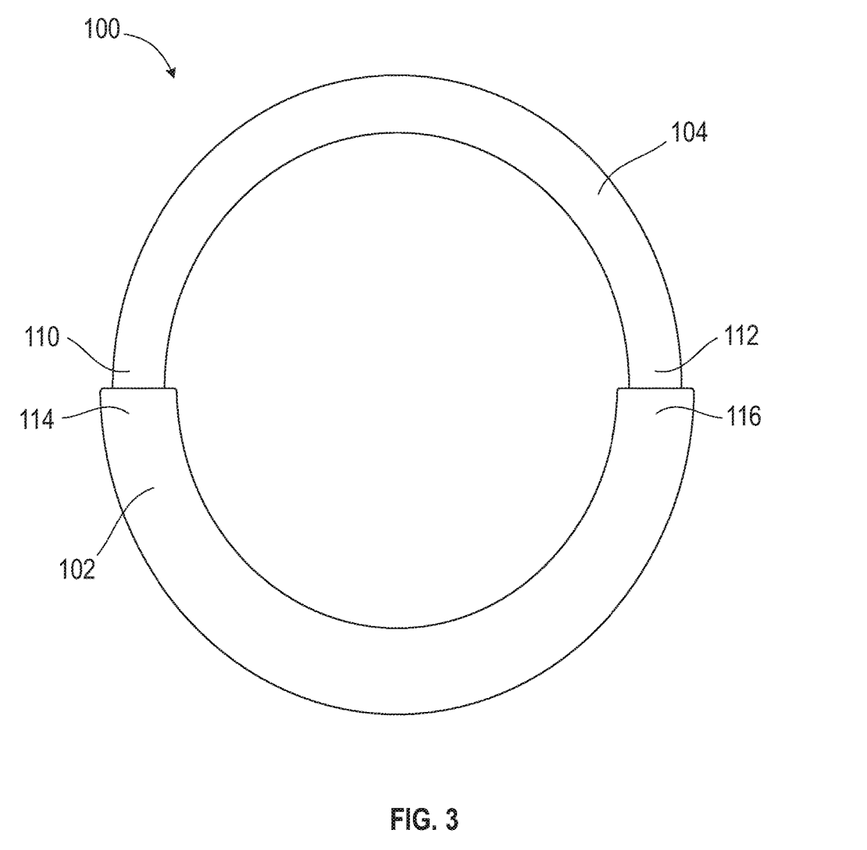
FIG. 3 shows an isolated top view of the head circumference measurement device shown in FIG. 1 showing a receiver segment and an adjustment segment assembled.
Figure 5:
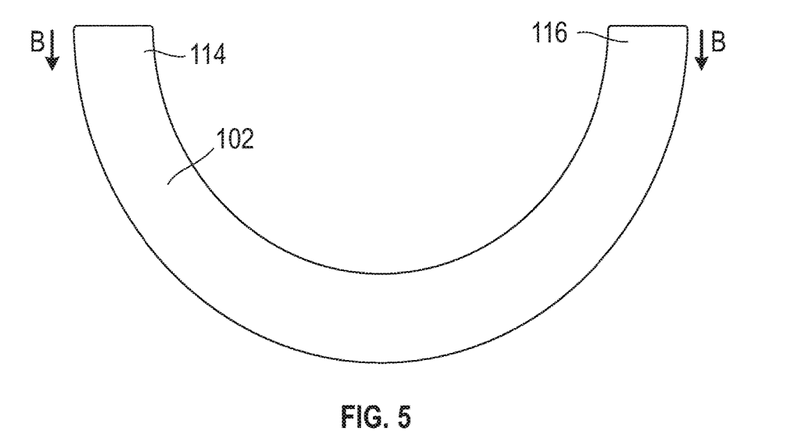
FIG. 5 shows an exploded top view of the receiver segment shown in FIG. 3.
Figure 6:
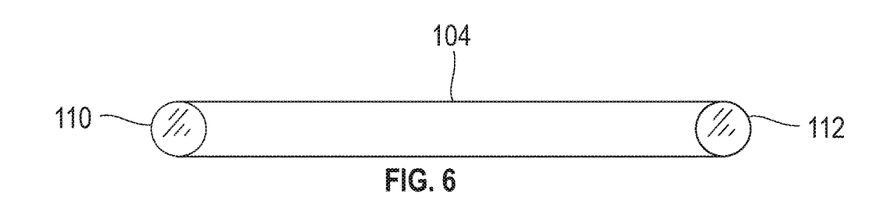
FIG. 6 shows a front view of the adjustment segment as viewed along sight line A shown in FIG. 4.
Figure 7:
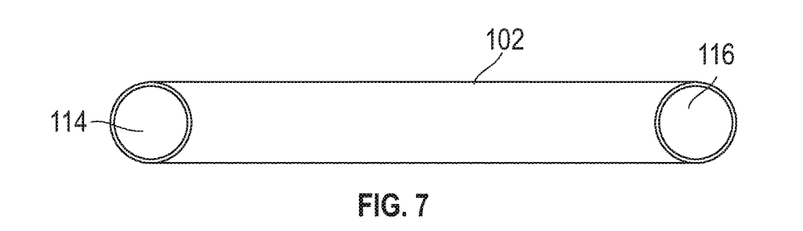
FIG. 7 shows a front view of the receiver segment as viewed along sight line B in FIG. 5.

The generally circumferential body 100 includes a receiver segment 102 that has a flexible, curved elongated geometry extending between a base end receiver 114 and an adjustment end receiver 116. The receiver segment 102 has a first length, for example about 30cm. The receiver segment 102 can include a tubular geometry with a hollow core extending between the receiver segment base end 114 and the receiver segment adjustment end 116. The receiver segment adjustment end receiver 116 can have an inner circumference of about 2 cm and correspondingly an inner diameter of about 0.6 cm. The receiver segment base end receiver 114 and the receiver segment adjustment end receiver 116 can have a common diameter.

Figure 4:
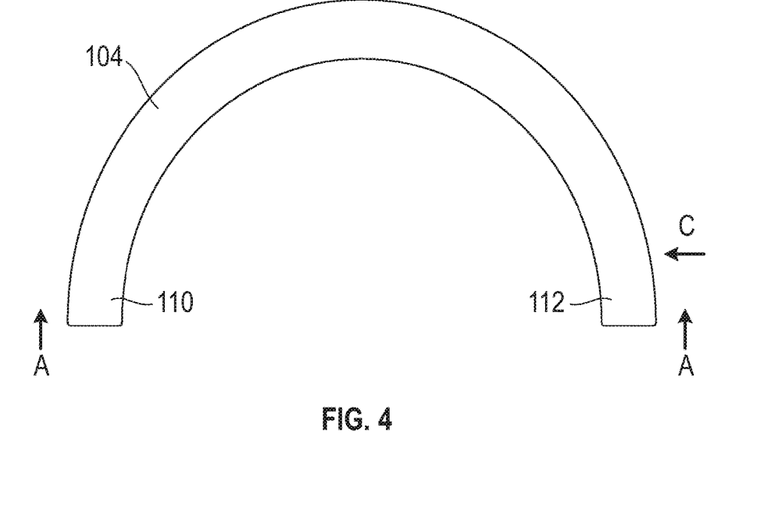
FIG. 4 shows an exploded top view of the adjustment segment shown in FIG. 3.

The generally circumferential body 100 also has an adjustment segment 104 that has a flexible, curved elongated geometry extending between a base end 110 and a measurement end 112. The adjustment segment 104 has a second length that can be longer than the receiver segment 102 first length. For example, the adjustment segment 104 can be about 60 cm. As illustrated, particularly in FIG. 6, the adjustment segment 104 can have a solid construction between the base end 110 and the measurement end 112.

The adjustment segment base end 110 and measurement end 112 can have diameters that are narrower than the receiver segment base end receiver 114 and adjustment end receiver 116 diameter. For example, the adjustment segment measurement end 112 can have an outer circumference of about 1.75 cm and correspondingly an outer diameter of about 0.5 cm. The adjustment segment base end 110 and the adjustment segment measurement end 112 comprise a common diameter.

The receiver segment 102 can have a greater arc circumference than the adjustment segment 104.

The adjustment segment base end 110 is fixed with the receiver segment base end receiver 114, for example through a friction fit or adhesive. The adjustment segment measurement end 112 is adjustably inserted into the receiver segment sliding end receiver 116 and can be secured together with a fastener, for example with a notch or a latch. The adjustment segment measurement end 112 is telescopically received within the receiver segment adjustment end receiver 116, such that the generally circumferential body 100 has a range of circumference between about 30 cm and about 60 cm.

Figure 1:
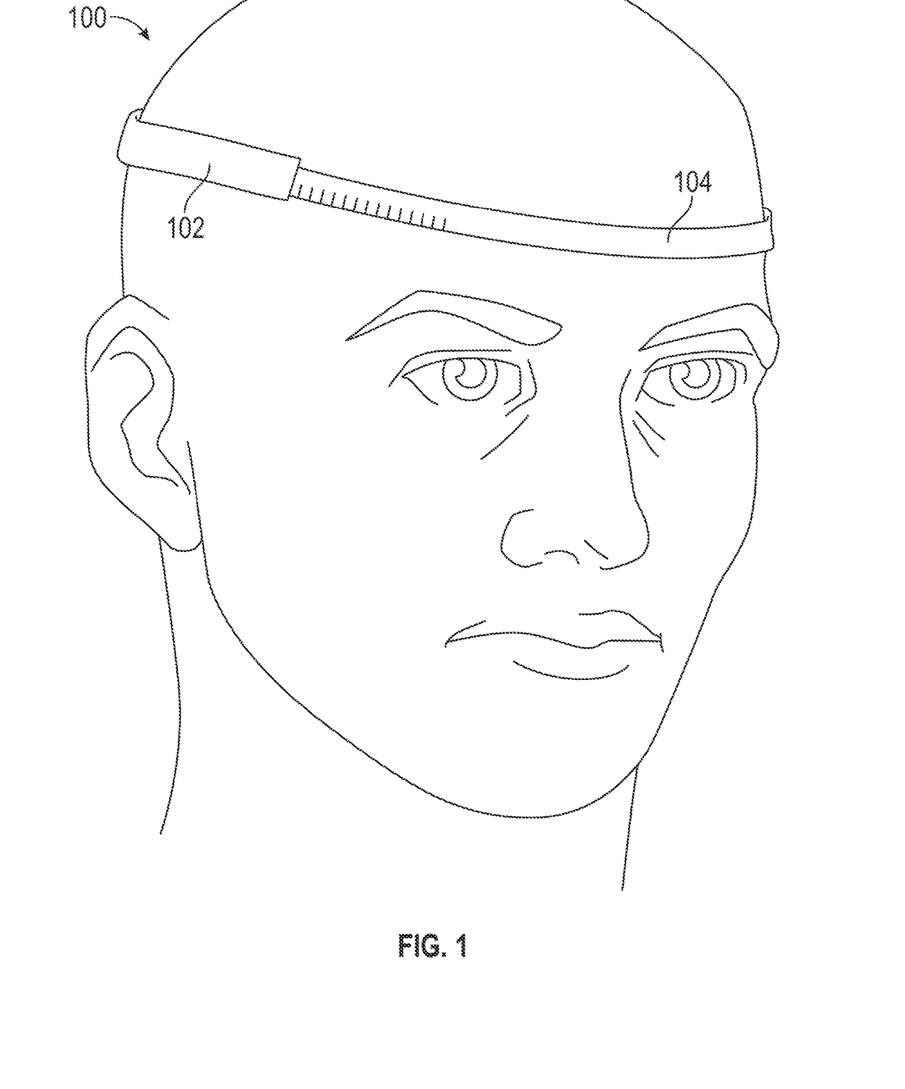
FIG. 1 shows a perspective view of a head circumference measurement device in use around a human head, according to an example embodiment of the present disclosure.
Figure 2:
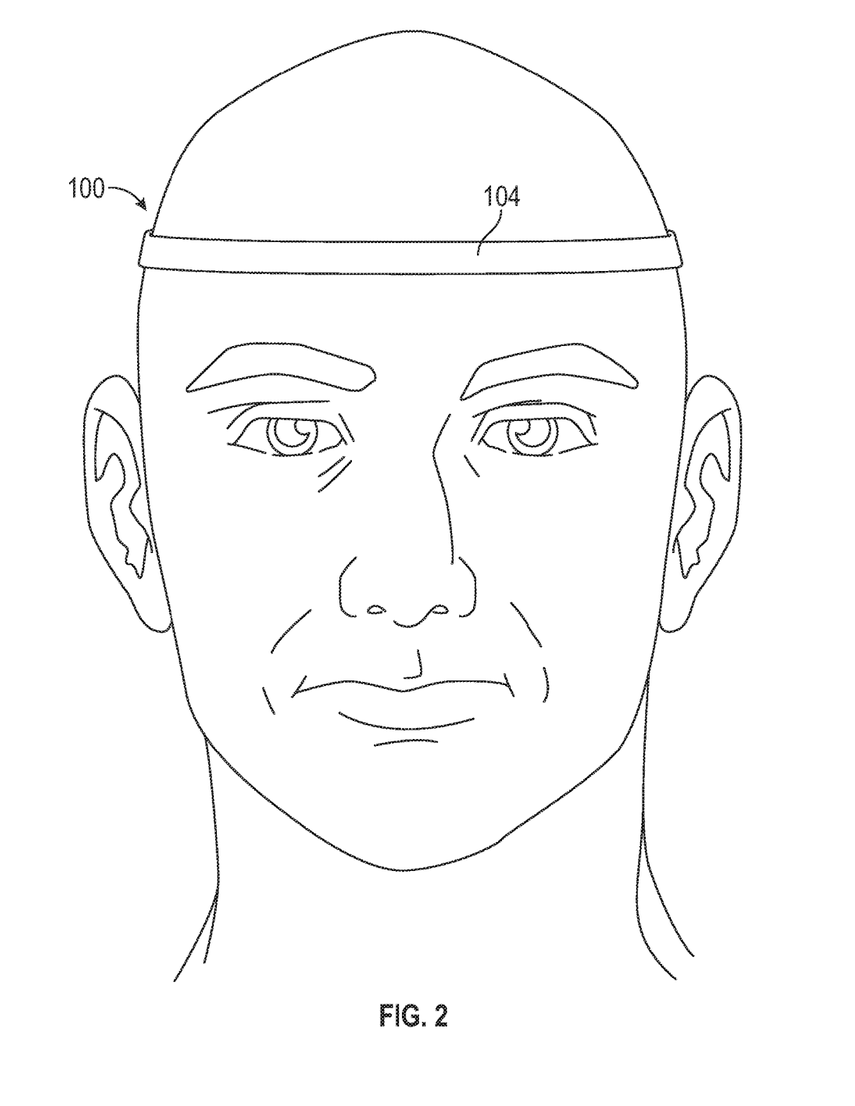
FIG. 2 shows a front view of the head circumference measurement device shown in FIG. 1.
Figure 8:
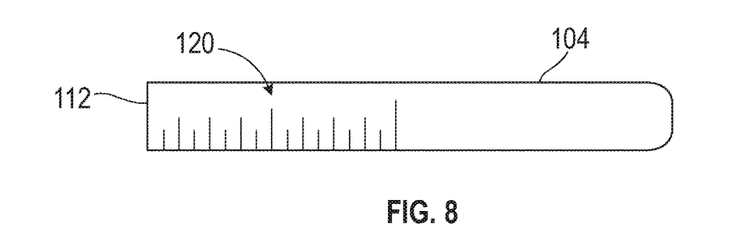
FIG. 8 shows a side view of the adjustment segment as viewed along sight line C in FIG. 4.

As particularly illustrated in FIGS. 1 and 8, the adjustment segment 104 has a measurement indicator 120 extending a predefined distance from the measurement end 112 toward the base end 110. The adjustment segment measurement indicator 120 has a series of evenly-spaced visual features, for example a series of evenly-spaced marks. The visual measurement indicator 120 is operable with respect to the receiver segment adjustment end receiver 116, such that as the adjustment segment measurement end 112 is telescopically inserted or removed from the receiver segment adjustment end 116, the visual measurement indicator aligns with the receiver segment adjustment end to provide a specific measurement.

Figure 9:
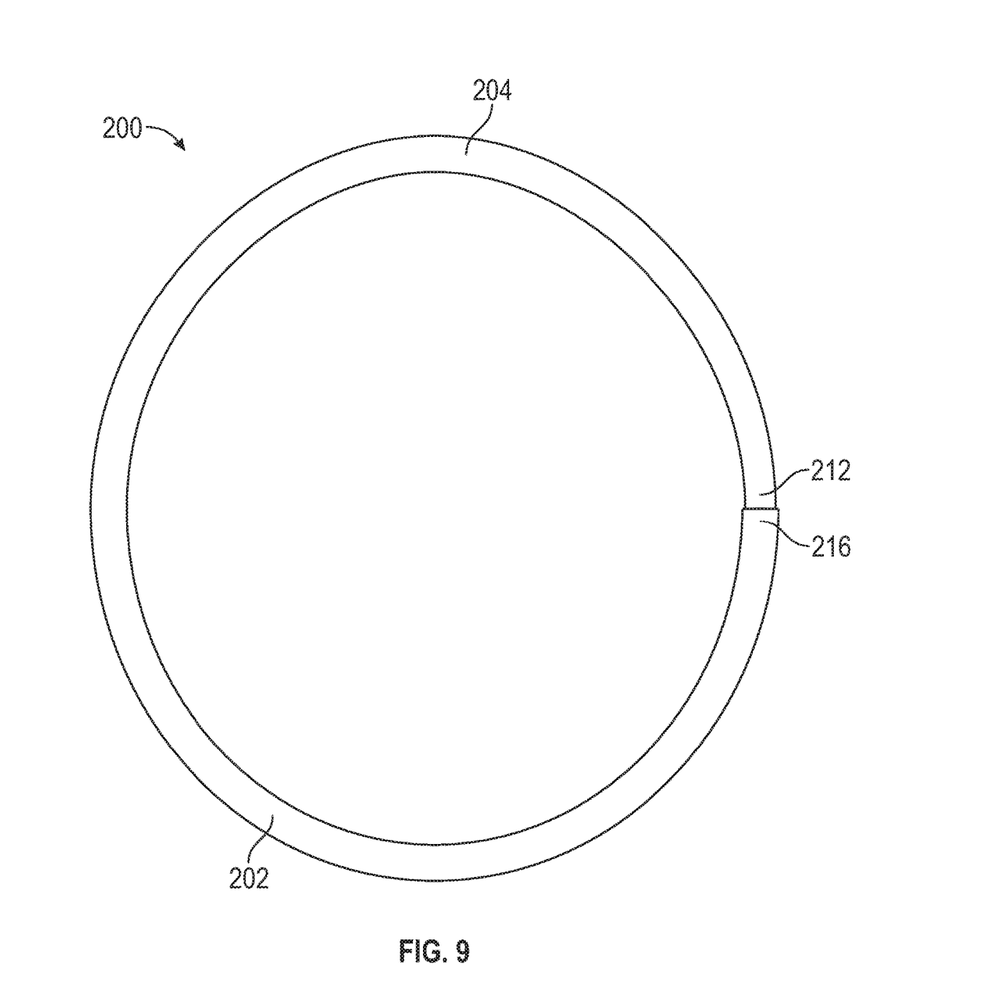
FIG. 9 shows an isolated top view of a head circumference measurement device according to another example embodiment of the present disclosure.
Figure 10:
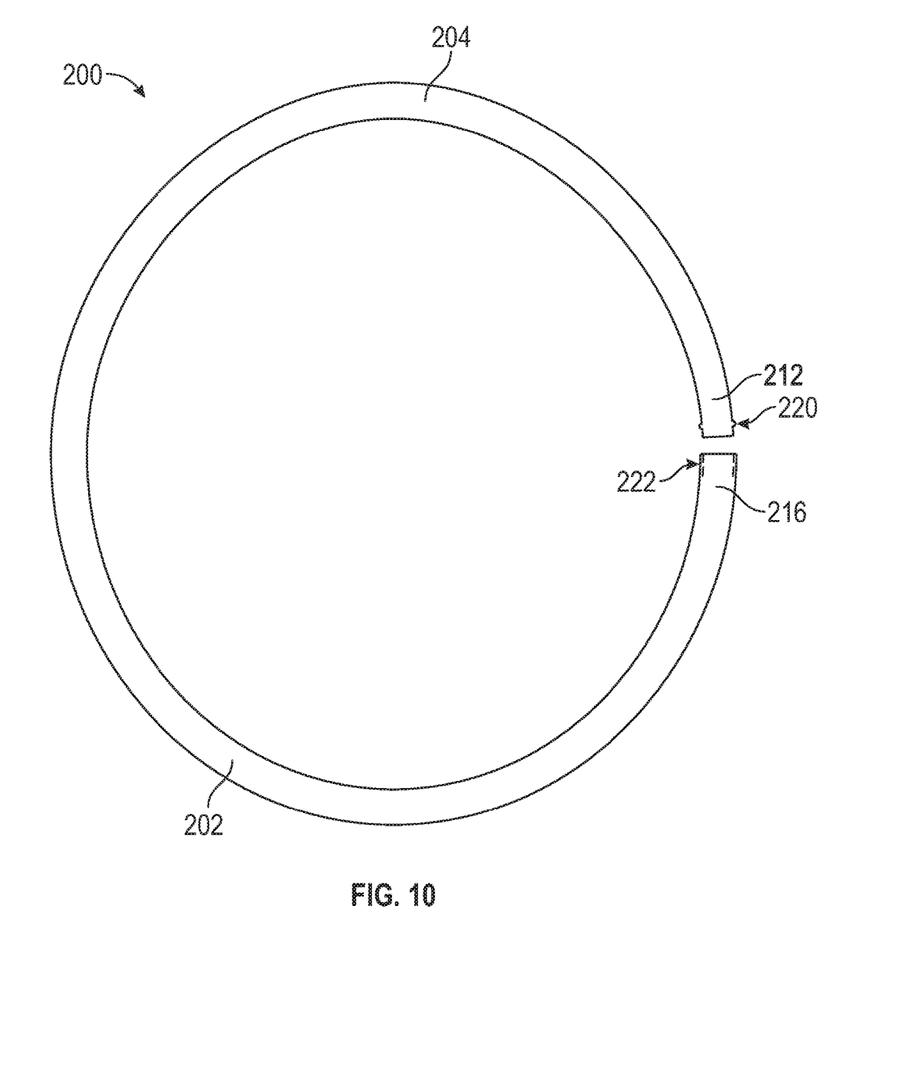
FIG. 10 shows an exploded top view of the head circumference measurement device shown in FIG. 9.

FIGS. 9 and 10 illustrate another head circumference measurement device 200 which has a generally similar structure and performs a similar function to the device described in FIGS. 1-8. While structurally generally similar to the device in FIGS. 1-8, instead of having separate receiver and adjustment segments, the illustrated measurement device 200 is a single unitary body. An illustrated receiver segment 202 and an adjustment segment 204 are sections of the same single structure. The receiver segment 202 includes an adjustment end 216 to receive a measurement end 212 of the adjustment segment 204, similarly to the device described in FIGS. 1-8.

Similarly to the device described in FIGS. 1-8, the adjustment segment 204 has a similar measurement indicator extending a predefined distance from the measurement end 212, and telescopically inserting into the adjustment end 216 of the receiver segment 202 to indicate circumference during measurement. The diameter of the receiver opening (not shown) of the adjustment end 216 of the receiver segment 202, and the diameter of the measurement end 212 of the adjustment segment 204, can have similar geometry and measurements to the device described in FIGS. 1-8.

As illustrated in FIG. 10, the device 200 can have a stopper assembly to releasably maintain the measurement end 212 of the adjustment segment 204 releasably inserted within the adjustment end 216 of the receiver segment 202. An example stopper assembly can include releasably engageable stoppers which can be pushed past each other when the measurement end 212 is inserted into the adjustment end 216, but can also be reversibly pulled in the opposite direction with enough force to remove the measurement end from the adjustment end. The illustrated stoppers can include a raised stopper 220 on the outer circumference of the measurement end 212 of the adjustment segment 204 and a raised stopper 222 on the inner circumference of the adjustment end 216 of the receiver segment 202. The illustrated stoppers 220, 222 can be continuously or non-continuously circumferential in geometry, as long as they can releasably engage each other and maintain the measurement end 212 within the adjustment end 216 without sufficient pulling force.

Similarly to the device described in FIGS. 1-8, when the measurement end 212 is inserted into the adjustment end 216, the adjustment segment 204 and receiver segment 202 telescope with respect to each other to provide a measurement indication. Preferably, the outer diameter of the stopper assembly 220 of the measurement end 212 is slidably engagable with the inner diameter of the adjustment end 216 of the receiver segment 202. Preferably, the inner diameter of the stopper assembly 222 of the adjustment end 216 is slidably engagable with the outer diameter of the measurement end 212 of the adjustment segment 204. Preferably, as the measurement end 212 is telescopically slid within the adjustment end 216, the stoppers 220, 222 engage the corresponding surfaces of the adjustment end 216 and the measurement end 212 with enough friction to maintain position if a user lets go of one of the ends, but also allow further telescopic movement if pulled or pushed with additional force.

Although specific embodiments of the disclosure have been described, numerous other modifications and alternative embodiments are within the scope of the disclosure. For example, any of the functionality described with respect to a particular device or component may be performed by another device or component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

What is claimed is:

1. A measurement device for measuring the circumference of a human head, the measurement device comprising:
   a generally circumferential body that fits around a human head, the generally circumferential body comprising:
      a receiver segment comprising an elongated geometry, the receiver segment comprising an adjustment end receiver, the receiver segment being flexible; and
      an adjustment segment comprising a measurement end, the adjustment segment measurement end comprising a diameter that is narrower than the receiver segment adjustment end receiver, the adjustment segment comprising a visual measurement indicator extending from the measurement end, the adjustment segment being flexible, wherein the adjustment segment measurement end is adjustably inserted into the receiver segment adjustment end receiver, wherein the visual measurement indicator is operable with respect to the receiver segment adjustment end receiver.

2. The measurement device of claim 1, wherein the adjustment segment and the receiver segment comprise a unitary construction.

3. The measurement device of claim 1, wherein the adjustment segment measurement indicator comprises a series of evenly-spaced visual features.

4. The measurement device of claim 1, wherein the adjustment segment measurement indicator comprises a series of evenly-spaced notches.

5. The measurement device of claim 1, wherein the adjustment segment further comprises a base end with a diameter and the adjustment segment measurement end comprises a diameter common with the base end diameter.

6. The measurement device of claim 5, wherein the receiver segment comprises a base end receiver, wherein the adjustment segment base end is fixed within the receiver segment base end receiver through a friction fit.

7. The measurement device of claim 6, wherein the adjustment segment base end is fixed within the receiver segment base end receiver through adhesive.

8. The measurement device of claim 6, wherein the receiver segment comprises a hollow core extending between the receiver segment base end receiver and the receiver segment adjustment end receiver.

9. The measurement device of claim 6, wherein the receiver segment base end receiver and the receiver segment adjustment end receiver comprise a common diameter.

10. The measurement device of claim 1, wherein the receiver segment is about 30 cm in length.

11. The measurement device of claim 1, wherein the adjustment segment is about 32 cm in length.

12. The measurement device of claim 1, wherein the adjustment segment measurement end is telescopically received within the receiver segment adjustment end receiver.

13. The measurement device of claim 12, wherein the generally circumferential body comprises a range of circumference between about 30 cm and about 60 cm.

14. The measurement device of claim 1, wherein the receiver segment adjustment end receiver comprises an inner circumference of about 2 cm.

15. The measurement device of claim 1, wherein the receiver segment adjustment end receiver comprises an inner diameter of about 0.6 cm.

16. The measurement device of claim 1, wherein the adjustment segment measurement end comprises an outer circumference of about 1.75 cm.

17. The measurement device of claim 1, wherein the adjustment segment measurement end comprises an outer diameter of about 0.5 cm.

18. The measurement device of claim 1, wherein the measurement device is comprised of antimicrobial plastic.

19. The measurement device of claim 1, wherein the generally circumferential body comprises a general D-shape with the receiver segment comprising a larger arc circumference than the adjustment segment.

20. The measurement device of claim 1, further comprising a stopper assembly configured to releasably maintain the adjustment segment within the receiver segment.

* * * * *